(12) United States Patent
Alaparthi et al.

(10) Patent No.: US 11,505,549 B2
(45) Date of Patent: Nov. 22, 2022

(54) PROCESS FOR PREPARATION OF DEUTETRABENAZINE

(71) Applicant: Lakshmi Prasad Alaparthi, Gujarat (IN)

(72) Inventors: Lakshmi Prasad Alaparthi, Vadodara (IN); Uday Sharma, Gujarat (IN); Gangireddy Kamalakar Reddy, Gujarat (IN)

(73) Assignee: Lakshmi Prasad Alaparthi, Vadodara (IN)

( * ) Notice: Subject to any disclaimer, the term of this patent is extended or adjusted under 35 U.S.C. 154(b) by 0 days.

(21) Appl. No.: 16/966,898

(22) PCT Filed: Jan. 30, 2019

(86) PCT No.: PCT/IN2019/050070
§ 371 (c)(1),
(2) Date: Aug. 2, 2020

(87) PCT Pub. No.: WO2019/150387
PCT Pub. Date: Aug. 8, 2019

(65) Prior Publication Data
US 2021/0047317 A1    Feb. 18, 2021

(30) Foreign Application Priority Data
Feb. 1, 2018  (IN) .............................. 201821003879

(51) Int. Cl.
*C07D 455/06* (2006.01)

(52) U.S. Cl.
CPC ........ *C07D 455/06* (2013.01); *C07B 2200/13* (2013.01)

(58) Field of Classification Search
CPC .................................................... C07D 455/06
See application file for complete search history.

(56) References Cited

U.S. PATENT DOCUMENTS 3,823,148 A * 7/1974 Jansen ................. C07D 217/02
546/144
2015/0152099 A1* 6/2015 Zhang .................. C07D 217/04
546/95

FOREIGN PATENT DOCUMENTS

WO    WO-2017182916 A1 * 10/2017 ........... C07D 455/06

OTHER PUBLICATIONS

Solecka "New Derivatives of 3,4-Dihydroisoquinoline-3-carboxylic Acid with Free-Radical Scavenging, D-Amino Acid Oxidase, Acetylcholinesterase and Butyrylcholinesterase Inhibitory Activity" Molecules 2014, 19, 15866-15890.*

* cited by examiner

*Primary Examiner* — David K O'Dell
(74) *Attorney, Agent, or Firm* — Mark M. Friedman

(57) ABSTRACT

A novel process for preparation of Deutetrabenazine ((RR, SS)-1,3,4,6,7-11b-Hexahydro-9,10-di(methoxy-$d_6$)-3-(2-methylpropyl)-2H-benzo [a] quinolizin-2-one) of formula I comprises of methylation of N-(2-(3,4-dihydroxy-phenyl)-ethyl)-formamide compound of formula III with deuteriated methanol ($CD_3OD$ or $CD_3OH$) to obtain $d_6$-N-(2-(3,4-dimethoxy-phenyl)-ethyl)-formamide compound of formula IV; cyclization of $d_6$-N-(2-(3,4-dimethoxy-phenyl)-ethyl)-formamide in presences of dehydrating agent to obtain $d_6$-6,7-Dimethoxy-3,4-dihydroisoquinoline compound of formula V; reacting $d_6$-6,7-Dimethoxy-3,4-dihydroisoquinoline compound of formula V with 2-acetyl-N,N,N,4-tetramethyl-1-pentanaminium iodide compound of formula VI.

6 Claims, No Drawings

PROCESS FOR PREPARATION OF DEUTETRABENAZINE

FIELD OF THE INVENTION

The present invention relates to a process for preparation of Deutetrabenazine ((RR, SS)-1,3,4,6,7-11b-Hexahydro-9,10-di(methoxy-$d_6$)-3-(2-methylpropyl)-2H-benzo [a] quinolizin-2-one) of formula I.

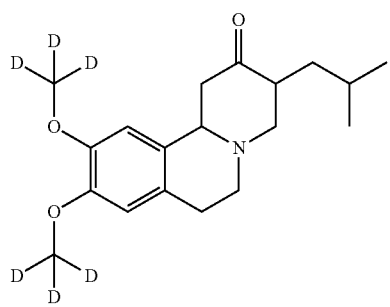

BACKGROUND OF THE INVENTION

Deutetrabenazine is a deuterated analog of tetrabenazine (I) which has improved pharmacokinetic properties when compared to the non-deuterated drug. Currently the New Drug Application (NDA) for deutetrabenazine has been accepted by the U.S. Food and Drug Administration (FDA) for the treatment of chorea associated with Huntington disease. Deutetrabenazine is a vesicular monoamine transporter 2 (VMAT2) inhibitor indicated for the treatment of chorea associated with Huntington's disease.

Deutetrabenazine is chemically known as (RR, SS)-1,3,4,6,7-11b-Hexahydro-9,10-di(methoxy-$d_6$)-3-(2-methylpropyl)-2H-benzo [a] quinolizin-2-one.

The U.S. Pat. No. 8,524,733 discloses deutetrabenazine and U.S. Pat. No. 3,045,021 discloses process for preparation of tetrabenazine.

The U.S. Pat. No. 8,524,733, provides process for preparation of deutetrabenazine by reaction of d6-6,7-Dimethoxy-3,4-dihydroisoquinoline and (2-acetyl-4-methyl-pentyl)-tri methyl-ammonium iodide (V) in ethanol. The product is isolated by column chromatography in yield of 35%. The intermediate d6-6,7-Dimethoxy-3,4-dihydroisoquinoline is prepared by series of reaction wherein (E)-4-(2-nitrovinyl) benzene-1,2-diol is reacted with d3-Iodomethane to produce d6-(E)-1,2-Dimethoxy-4-(2-nitrovinyl)benzene which undergoes reduction in presence of lithium aluminum hydride to give 2-(3,4-d6-di methoxyphenyl) ethanamine which further reacts with hexamethylenetetramine in presence of acetic acid/trifluoroacetic acid to give the intermediate d6-6,7-Dimethoxy-3,4-dihydroisoquinoline. The process utilizes expensive reagents like d3-Iodomethane, tedious technique of column chromatography resulting in low yields hence is not industrially feasible.

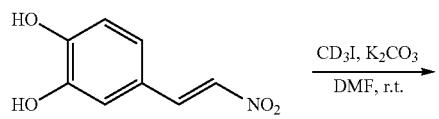

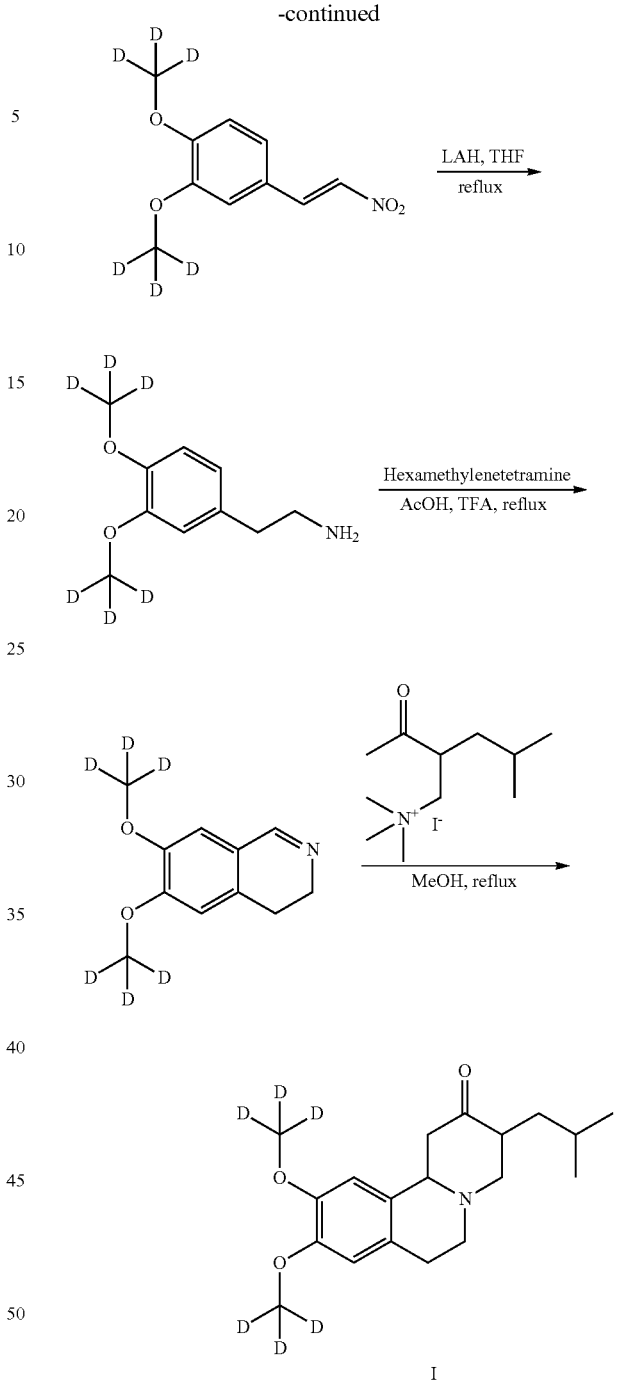

Another patent application US 20150152099 describes process for preparation of deutetrabenazine by reaction of d6-6,7-Di methoxy-3,4-dihydroisoquinoline and (2-acetyl-4-methyl-pentyl)-tri methyl-ammonium iodide (V) in various solvents. The intermediate d6-6,7-Dimethoxy-3,4-dihydroisoquinoline is prepared by series of reaction wherein dopamine hydrochloride reacts with ethyl formate to give N-(2-(3,4-di hydroxy-phenyl)-ethyl)-formamide which reacts further with d3-Iodomethane to produce deuterated compound which is cyclized in presence of phosphoryl chloride to give d6-6,7-Dimethoxy-3-dihydro isoquinoline hydrochloride. The process utilizes expensive reagents like d3-Iodomethane.

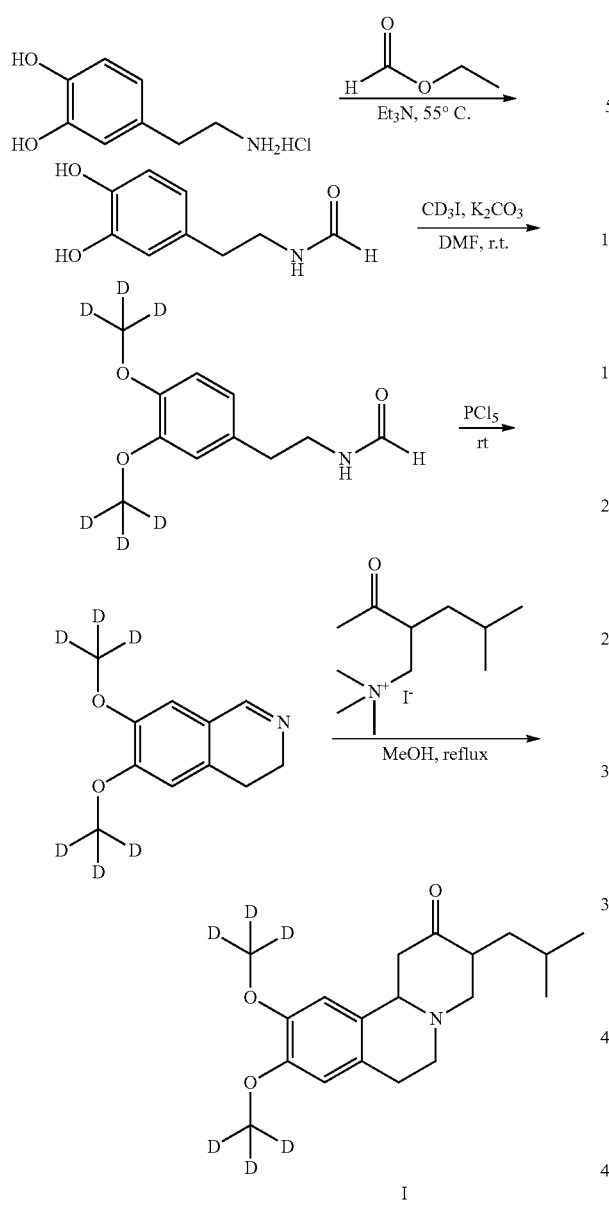

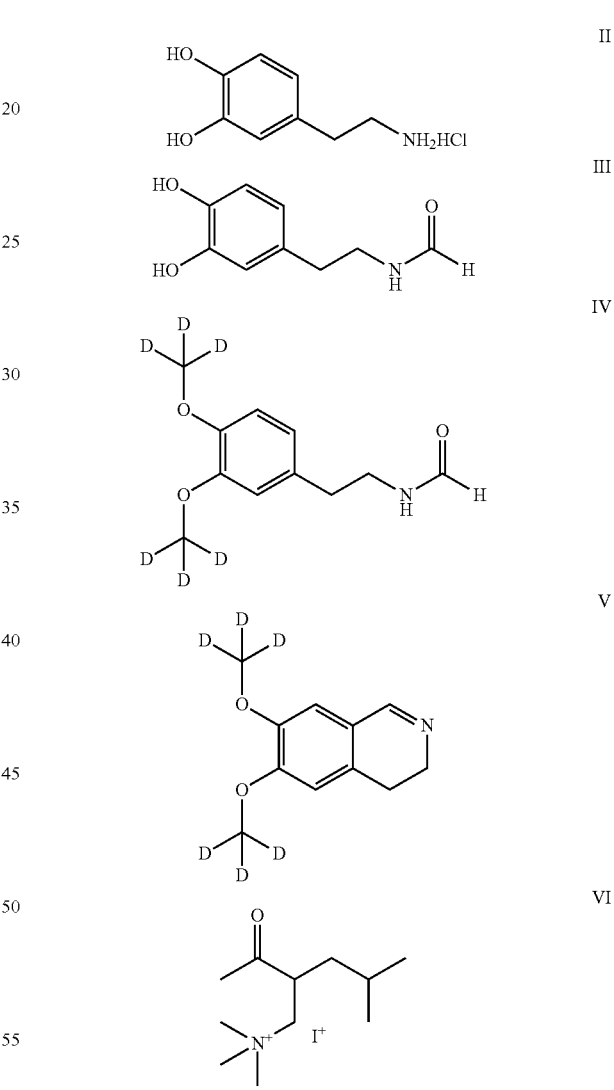

phenyl)-ethyl)-formamide compound of formula III; (ii) methylation of N-(2-(3,4-dihydroxy-phenyl)-ethyl)-formamide compound of formula III with deuterated methanol (CD$_3$OD or CD$_3$OH) to obtain d$_6$-N-(2-(3,4-dimethoxyphenyl)-ethyl)-formamide compound of formula IV; (iii) cyclization of d$_6$-N-(2-(3,4-dimethoxy-phenyl)-ethyl)-formamide in presences of dehydrating agent to obtain d$_6$-6,7-Dimethoxy-3,4-dihydroisoquinoline compound of formula V; (iv) reacting d$_6$-6,7-Dimethoxy-3,4-dihydroisoquinoline compound of formula V with 2-acetyl-N,N,N,4-tetramethyl-1-pentanaminium iodide compound of formula VI to obtain (RR, SS)-1,3,4,6,7-11b-Hexahydro-9,10-di (methoxy-d$_6$)-3-(2-methylpropyl)-2H-benzo [a] quinolizin-2-one (Deutetrabenazine) compound of formula I.

The present invention is directed to provide novel process for the preparation of deutetrabenazine of formula I which is efficient, industrially viable wherein reaction conditions are mild and simple for operation, less expensive cost effective process.

SUMMARY OF THE INVENTION

A primary object of the present invention is to provide an novel process for the preparation of (RR, SS)-1,3,4,6,7-11b-Hexahydro-9,10-di(methoxy-d$_6$)-3-(2-methylpropyl)-2H-benzo [a] quinolizin-2-one ((+/−)-d$_6$-Tetrabenazine) (Deutetrabenazine) of formula I and pharmaceutically acceptable salts thereof.

An object of the present invention is to provide novel process for the preparation of Deutetrabenazine compound of formula I comprising steps of: (i) reacting dopamine hydrochloride compound of formula II with ethyl formate in presences of triethylamine to obtain N-(2-(3,4-dihydroxy-phenyl)-ethyl)-formamide compound of formula III; (ii) cyclization of N-(2-(3,4-dihydroxy-phenyl)-ethyl)-formamide compound of formula III in presences of dehydrating agent to obtain 6,7-dihydroxy-3,4-dihydroisoquinoline compound of for- An object of the present invention is to provide novel process for the preparation of Deutetrabenazine formula I comprising steps of: (i) reacting dopamine hydrochloride compound of formula II with ethyl formate in presences of triethylamine to obtain N-(2-(3,4-dihydroxy-phenyl)-ethyl)-formamide compound of formula III; (ii) cyclization of N-(2-(3,4-dihydroxy-phenyl)-ethyl)-formamide compound of formula III in presences of dehydrating agent to obtain 6,7-dihydroxy-3,4-dihydroisoquinoline compound of formula VII; (iii) methylation of 6,7-dihydroxy-3,4-dihydroisoquinoline compound of formula VII with deuterated methanol (CD$_3$OD or CD$_3$OH) to obtain d$_6$-6,7-Dimethoxy-3,4-dihydroisoquinoline compound of formula V; (iv) reacting d$_6$-6,7-Dimethoxy-3,4-dihydroisoquinoline compound of formula V with 2-acetyl-N,N,N,4-tetramethyl-1-pentanaminium iodide compound of formula VI to obtain (RR, SS)-1,3,4,6,7-11b-Hexahydro-9,10-di (methoxy-d$_6$)-3-(2-methylpropyl)-2H-benzo [a] quinolizin-2-one (Deutetrabenazine) compound of formula I.

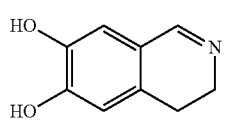

VII

An object of the present invention is to provide novel process for the preparation of d$_6$-N-(2-(3,4-dimethoxy-phenyl)-ethyl)-formamide compound of formula IV comprising: (i) reacting dopamine hydrochloride compound of formula II with ethyl formate in presences of triethylamine to obtain N-(2-(3,4-dihydroxy-phenyl)-ethyl)-formamide compound of formula III; (ii) methylation of N-(2-(3,4-dihydroxy-phenyl)-ethyl)-formamide compound of formula III with deuterated methanol (CD$_3$OD or CD$_3$OH) to obtain d$_6$-N-(2-(3,4-dimethoxy-phenyl)-ethyl)-formamide compound of formula IV.

An object of the present invention is to provide novel process for the preparation of d$_6$-6,7-Dimethoxy-3,4-dihydroisoquinoline formula V comprising: (i) reacting dopamine hydrochloride compound of formula II with ethyl formate in presences of triethylamine to obtain N-(2-(3,4-dihydroxy-phenyl)-ethyl)-formamide compound of formula III; (ii) cyclization of N-(2-(3,4-dihydroxy-phenyl)-ethyl)-formamide compound of formula III in presences of dehydrating agent to obtain 6,7-dihydroxy-3,4-dihydroisoquinoline compound of formula VII; (iii) methylation of 6,7-dihydroxy-3,4-dihydroisoquinoline compound of formula VII with deuterated methanol (CD$_3$OD or CD$_3$OH) to obtain d$_6$-6,7-Dimethoxy-3,4-dihydroisoquinoline compound of formula V.

DETAILED DESCRIPTION OF THE INVENTION

As used herein, the terms below have the meanings indicated.

The singular forms "a," "an," and "the" may refer to plural articles unless specifically stated otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

As used herein, the term "pharmaceutically acceptable salt" refers to those salts which are suitable for pharmaceutical use, preferably for use in the tissues of humans and lower animals without undue irritation, allergic response and the like. Pharmaceutically acceptable salts of amines, carboxylic acids, and other types of compounds, are well known in the art. For example, S. M. Berge, et al., describe pharmaceutically acceptable salts in detail in J Pharmaceutical Sciences, 66: 1-19 (1977), incorporated herein by reference. The salts are prepared in situ during the final isolation and purification of the compounds of the invention, or separately by reacting a free base or free acid function with a suitable reagent, as described generally below. For example, a free base function is reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzoate, bisulfate, borate, butyrate, camphorate, camphorsulfonate, citrate, cyclopentanepropionate, digluconate, dodecylsulfate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, nicotinate, nitrate, oleate, oxalate, palmitate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed by direct reaction with the drug carboxylic acid or by using counterions such as halide, hydroxide, carboxylate, sulfate, phosphate, nitrate, sulfonate and aryl sulfonate.

In the first embodiment the present invention provides process for preparation of Deutetrabenazine compound of formula I which includes the step of:

(i) reacting dopamine hydrochloride compound of formula II with ethyl formate in presences of Triethylamine to obtain N-(2-(3,4-dihydroxy-phenyl)-ethyl)-formamide compound of formula III;

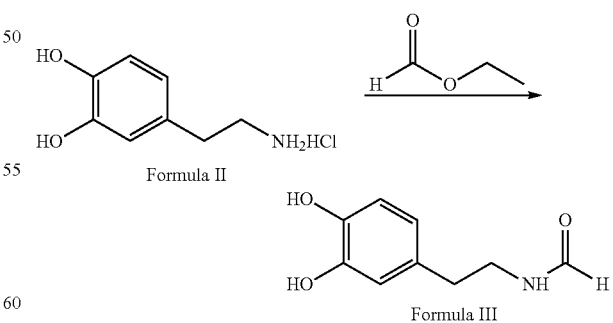

(ii) methylation of N-(2-(3,4-dihydroxy-phenyl)-ethyl)-formamide compound of formula III with deuterated methanol (CD$_3$OD or CD$_3$OH) to obtain d$_6$-N-(2-(3,4-dimethoxy-phenyl)-ethyl)-formamide compound of formula IV;

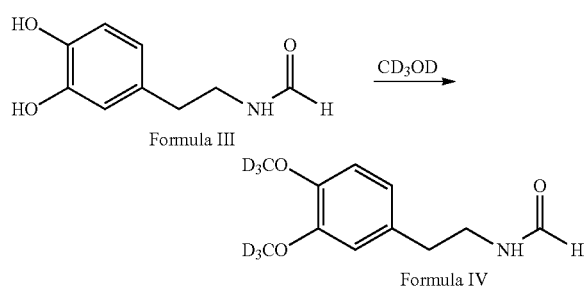

(iii) cyclization of d₆-N-(2-(3,4-dimethoxy-phenyl)-ethyl)-formamide in presences of dehydrating agent to obtain d₆-6,7-Dimethoxy-3,4-dihydroisoquinoline compound of formula V;

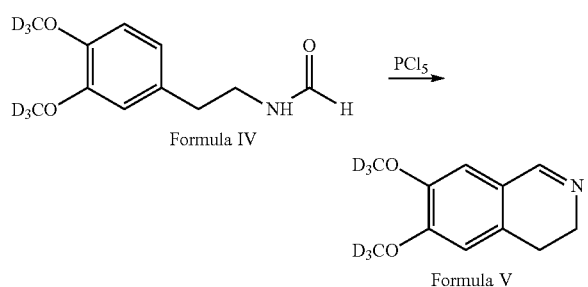

(iv) reacting d₆-6,7-Dimethoxy-3,4-dihydroisoquinoline compound of formula V with 2-acetyl-N,N,N,4-tetramethyl-1-pentanaminium iodide compound of formula VI to obtain (RR, SS)-1,3,4,6,7-11b-Hexahydro-9,10-di (methoxy-d₆)-3-(2-methylpropyl)-2H-benzo [a] quinolizin-2-one (Deutetrabenazine) compound of formula I.

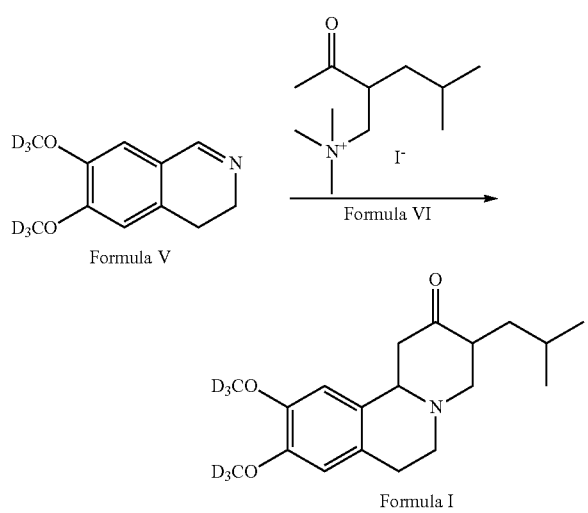

In the process of step (ii) for preparation of d₆-N-(2-(3, 4-dimethoxy-phenyl)-ethyl)-formamide compound of formula IV, N-(2-(3,4-dihydroxy-phenyl)-ethyl)-formamide compound of formula III is treated with a source of deuterated methyl selected from deuterated methanol, CD₃OD or CD₃OH etc. Further the process of step (ii) the reaction is carried out in presence of reagent selected from diethyl azodicarboxylate (DEAD), diisopropyl azodicarboxylate (DIAD), di-p-chlorobenzyl azodicarboxylate (DCAD), 1,1'-(Azodicarbonyl)dipiperidine (ADDA), Tetramethyl azodicarboxamide (TMAD in combination with triphenyl phosphine.

In the process of step (ii) the reaction is carried out in the presences of solvents selected from solvents selected from dichloromethane, ethylene dichloride, carbon tetrachloride, chloroform, tetrahydrofuran, benzene, toluene, N,N-dimethylformamide or mixture thereof. The reaction is carried out at an ambient temperature of −5° C. to 30° C. d₆-N-(2-(3, 4-dimethoxy-phenyl)-ethyl)-formamide compound of formula IV is isolated by techniques known in art like filtration, evaporation, concentration etc. Isolated d₆-N-(2-(3,4-dimethoxy-phenyl)-ethyl)-formamide compound of formula IV was obtained in a HPLC purity of greater than 90.0%.

In the process of step (iii), said dehydrating agent is selected from the group consisting of phosphorous oxy chloride, phosphorus pentachloride, and thionyl chloride.

In the process of step (iv) the reaction of d₆-6,7-Dimethoxy-3,4-dihydroisoquinoline compound of formula V with 2-acetyl-N,N,N,4-tetramethyl-1-pentanaminium iodide compound of formula VI is carried out in presence of solvent and a base. The solvent is selected from polar solvents like alcohols; methanol, ethanol, propanol, butanol, nitriles acetonitrile, propionitrile, acetone, tetrahydrofuran, dimethylformamide, dimethyl sulfoxide, glycol, dioxane, propanediol, butanediol, water or mixture thereof. The base is selected from organic or inorganic base; organic base are triethylamine or tributylamine etc. inorganic bases include hydroxide, alkoxides or carbonates, bicarbonates of alkali or alkaline earth metal like sodium hydroxide, potassium hydroxide, sodium methoxide, potassium methoxide, sodium carbonate, potassium carbonate, sodium bicarbonate etc. The reaction is carried out at a temperature of 30 to 60° C.

The above process is represented stepwise as shown below:

Scheme I

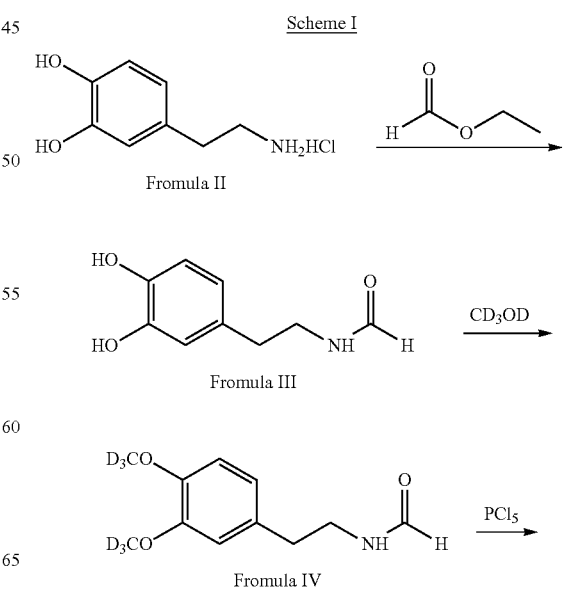

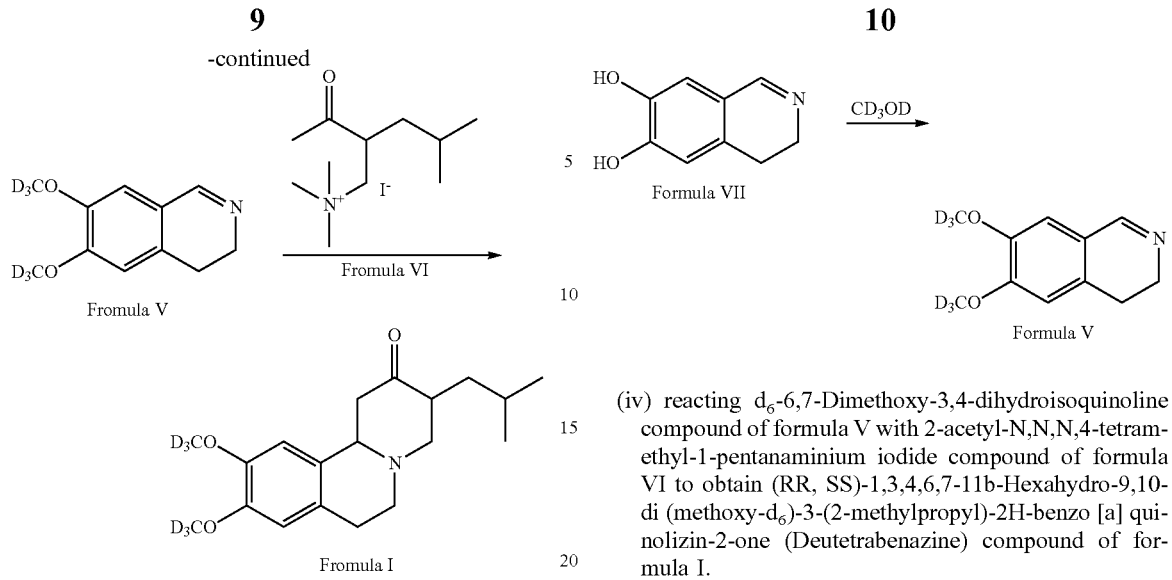

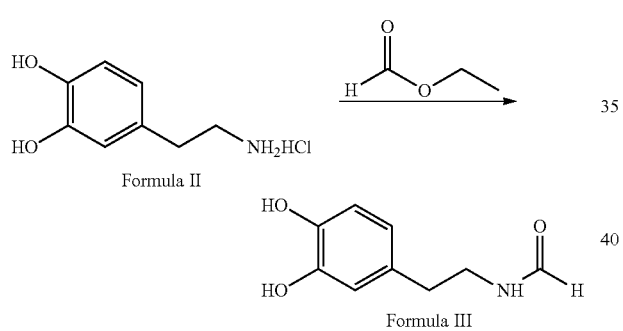

(ii) cyclization of N-(2-(3,4-dihydroxy-phenyl)-ethyl)-formamide compound of formula III in presences of dehydrating agent to obtain 6,7-dihydroxy-3,4-dihydroisoquinoline compound of formula VII;

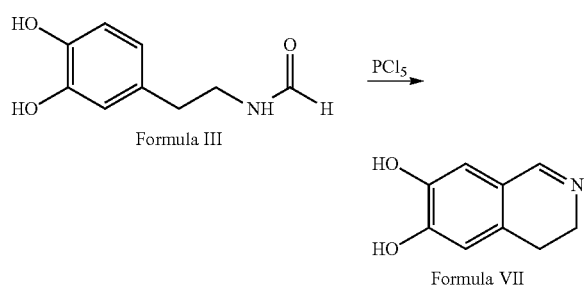

(iii) methylation of 6,7-dihydroxy-3,4-dihydroisoquinoline compound of formula VII with deuterated methanol (CD₃OD or CD₃OH) to obtain d₆-6,7-Dimethoxy-3,4-dihydroisoquinoline compound of formula V;

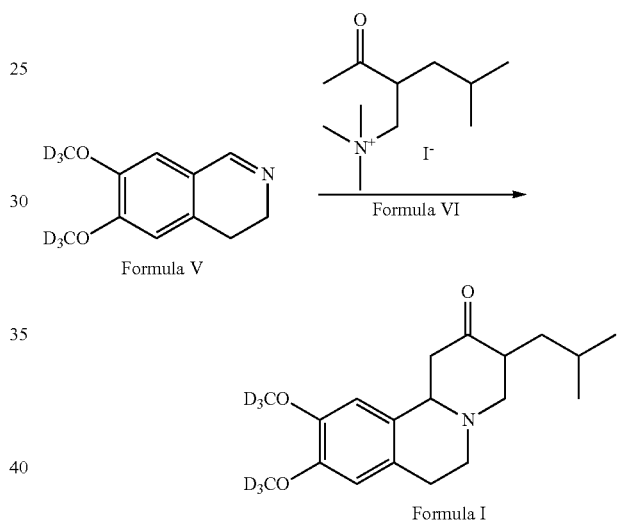

(iv) reacting d₆-6,7-Dimethoxy-3,4-dihydroisoquinoline compound of formula V with 2-acetyl-N,N,N,4-tetramethyl-1-pentanaminium iodide compound of formula VI to obtain (RR, SS)-1,3,4,6,7-11b-Hexahydro-9,10-di (methoxy-d₆)-3-(2-methylpropyl)-2H-benzo [a] quinolizin-2-one (Deutetrabenazine) compound of formula I.

In the process of step (ii), said dehydrating agent is selected from the group consisting of phosphorous oxy chloride, phosphorus pentachloride, and thionyl chloride.

In the process of step (iii) for preparation of d₆-6,7-Dimethoxy-3,4-dihydroisoquinoline compound of formula V, 6,7-dihydroxy-3,4-dihydroisoquinoline compound of formula VII is treated with a source of deuterated methyl selected from deuterated methanol, CD₃OD or CD₃OH etc. Further the process of step (ii) the reaction is carried out in presence of reagent selected from diethyl azodicarboxylate (DEAD), diisopropyl azodicarboxylate (DIAD), di-p-chlorobenzyl azodicarboxylate (DCAD), 1,1'-(Azodicarbonyl) dipiperidine (ADDA), Tetramethyl azodicarboxamide (TMAD in combination with triphenyl phosphine.

In the process of step (iii) the reaction is carried out in the presences of solvents selected from solvents selected from dichloromethane, ethylene dichloride, carbon tetrachloride, chloroform, tetrahydrofuran, benzene, toluene, N,N-dimethylformamide or mixture thereof. The reaction is carried out at an ambient temperature of −5° C. to 30° C. d₆-6,7-Dimethoxy-3,4-dihydroisoquinoline compound of formula V is isolated by techniques known in art like filtration, evaporation, concentration etc. Isolated d₆-6,7-Dimethoxy- 3,4-dihydroisoquinoline compound of formula V was obtained in a HPLC purity of greater than 90.0%.

In the process of step (iv) the reaction of $d_6$-6,7-Dimethoxy-3,4-dihydroisoquinoline compound of formula V with 2-acetyl-N,N,N,4-tetramethyl-1-pentanaminium iodide compound of formula VI is carried out in presence of solvent and a base. The solvent is selected from polar solvents like alcohols; methanol, ethanol, propanol, butanol, nitriles acetonitrile, propionitrile, acetone, tetrahydrofuran, dimethylformamide, dimethyl sulfoxide, glycol, dioxane, propanediol, butanediol, water or mixture thereof. The base is selected from organic or inorganic base; organic base are triethylamine or tributylamine etc. inorganic bases include hydroxide, alkoxides or carbonates, bicarbonates of alkali or alkaline earth metal like sodium hydroxide, potassium hydroxide, sodium methoxide, potassium methoxide, sodium carbonate, potassium carbonate, sodium bicarbonate etc. The reaction is carried out at a temperature of 30 to 60° C.

The above process is represented stepwise as shown below:

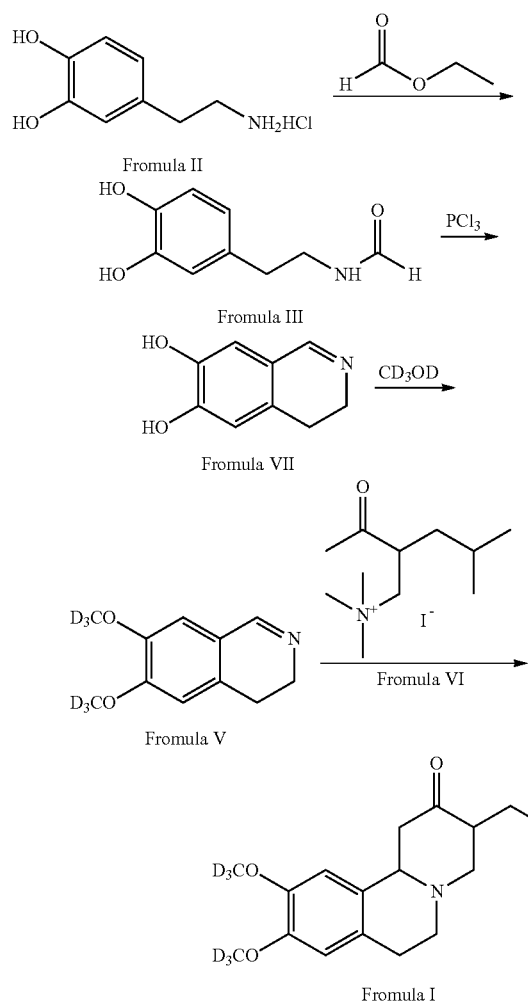

In the third embodiment the present invention provides process for preparation of $d_6$-N-(2-(3,4-dimethoxy-phenyl)-ethyl)-formamide compound of formula IV comprising:

methylation of N-(2-(3,4-dihydroxy-phenyl)-ethyl)-formamide compound of formula III with deuterated methanol ($CD_3OD$ or $CD_3OH$) to obtain $d_6$-N-(2-(3,4-dimethoxy-phenyl)-ethyl)-formamide compound of formula IV.

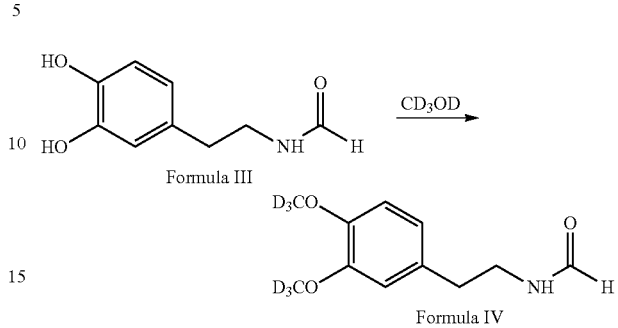

In the process of preparation of $d_6$-N-(2-(3,4-dimethoxy-phenyl)-ethyl)-formamide compound of formula IV, N-(2-(3,4-dihydroxy-phenyl)-ethyl)-formamide compound of formula III is treated with a source of deuterated methyl selected from deuterated methanol, $CD_3OD$ or $CD_3OH$ etc. Further the process of step (ii) the reaction is carried out in presence of reagent selected from diethyl azodicarboxylate (DEAD), diisopropyl azodicarboxylate (DIAD), di-p-chlorobenzyl azodicarboxylate (DCAD), 1,1'-(Azodicarbonyl) dipiperidine (ADDA), Tetramethyl azodicarboxamide (TMAD in combination with triphenyl phosphine.

In the process the reaction is carried out in the presences of solvents selected from solvents selected from dichloromethane, ethylene dichloride, carbon tetrachloride, chloroform, tetrahydrofuran, benzene, toluene, N,N-dimethyl-formamide or mixture thereof. The reaction is carried out at an ambient temperature of −5° C. to 30° C. $d_6$-N-(2-(3,4-dimethoxy-phenyl)-ethyl)-formamide compound of formula IV is isolated by techniques known in art like filtration, evaporation, concentration etc. Isolated $d_6$-N-(2-(3,4-dimethoxy-phenyl)-ethyl)-formamide compound of formula IV was obtained in a HPLC purity of greater than 90.0%.

In the fourth embodiment the present invention is to provide novel process for the preparation of $d_6$-6,7-Dimethoxy-3,4-dihydroisoquinoline formula V comprising:

(i) cyclization of N-(2-(3,4-dihydroxy-phenyl)-ethyl)-formamide compound of formula III in presences of dehydrating agent to obtain 6,7-dihydroxy-3,4-dihydroisoquinoline compound of formula VII;

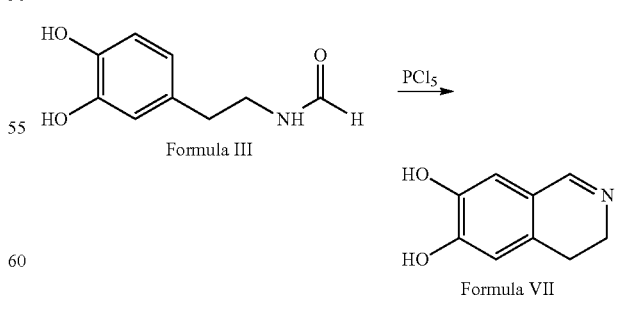

(ii) methylation of 6,7-dihydroxy-3,4-dihydroisoquinoline compound of formula VII with deuterated methanol ($CD_3OD$ or $CD_3OH$) to obtain $d_6$-6,7-Dimethoxy-3,4-dihydroisoquinoline compound of formula V.

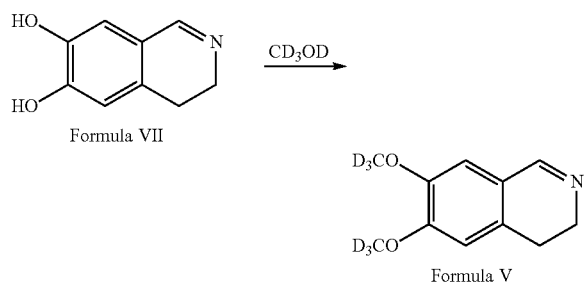

Formula VII → Formula V

In the process of step (i), said dehydrating agent is selected from the group consisting of phosphorous oxy chloride, phosphorus pentachloride, and thionyl chloride.

In the process of step (ii) for preparation of $d_6$-6,7-Dimethoxy-3,4-dihydroisoquinoline compound of formula V, 6,7-dihydroxy-3,4-dihydroisoquinoline compound of formula VII is treated with a source of deuterated methyl selected from deuterated methanol, $CD_3OD$ or $CD_3OH$ etc. Further the process of step (ii) the reaction is carried out in presence of reagent selected from diethyl azodicarboxylate (DEAD), diisopropyl azodicarboxylate (DIAD), di-p-chlorobenzyl azodicarboxylate (DCAD), 1,1'-(Azodicarbonyl) dipiperidine (ADDA), Tetramethyl azodicarboxamide (TMAD in combination with triphenyl phosphine.

In the process of step (ii) the reaction is carried out in the presences of solvents selected from solvents selected from dichloromethane, ethylene dichloride, carbon tetrachloride, chloroform, tetrahydrofuran, benzene, toluene, N,N-dimethylformamide or mixture thereof. The reaction is carried out at an ambient temperature of −5° C. to 30° C. $d_6$-6,7-Dimethoxy-3,4-dihydroisoquinoline compound of formula V is isolated by techniques known in art like filtration, evaporation, concentration etc. Isolated $d_6$-6,7-Dimethoxy-3,4-dihydroisoquinoline compound of formula V was obtained in a HPLC purity of greater than 90.0%.

In various embodiments, the solvent is an aprotic solvent, a protic solvent, a polar solvent, a non-polar solvent, an ionic solvent. Suitable solvent is selected from but not limited to dioxane, tetrahydrofuran, acetone, hexane, benzene, toluene, 1,4-dioxane, chloroform, diethyl ether, dichloromethane, tetrahydrofuran, ethyl acetate, acetone, dimethylformamide, acetonitrile, dimethyl sulfoxide, n-butanol, isopropanol, n-propanol, ethanol, methanol, water, ketones, diols, triols, esters, amides, ethers, hydrocarbons, polar aprotic solvents, polar solvents, chloro solvents, nitriles or mixtures thereof.

Polar aprotic solvents such as acetone, DMF, acetonitrile, DMSO, sulfolane; alcohols such as methanol, ethanol, propanol, butanol; chloro solvents like methylene chloride, chloroform, monochlorobenzene, MDC, and EDC and ethylene chloride; hydrocarbon solvents like toluene, xylene, heptane, cyclohexane and hexane, and combinations thereof.

The process of the invention is illustrated with reference to the following Examples and is not intended to limit the scope of the invention. Any permutations and modifications in the process are possible keeping in mind the scope of the invention.

EXAMPLE 1

Preparation of N-(3,4-dihydroxyphenethyl)formamide

Triethylamine (110.0 mL, 789.21 mmol) was added to a suspension of 4-(2-aminoethyl)benzene-1,2-diol hydrochloride (100.0 g, 527.31 mmol) in ethyl formate (500 mL) at 0° C. Reaction mixture was stirred at 55° C. for 15 hours. After completion of reaction (monitored by TLC) excess ethyl formate was removed under reduced pressure at 45° C. The resulting residue was diluted with water (500 mL) and stirred at room temperature for 1 hour. The solid separated was filtered off and washed with water (3×100 mL). Isolated solid was dried at 65° C. for 12 hours yielding 62.0 g pure N-(3,4-dihydroxyphenethyl)formamide as a beige solid (Yield: 65%). Purity by HPLC: 99%

EXAMPLE 2

Preparation of D6-N-(3,4-dimethoxyphenethyl)formamide

D4-Methanol (25.0 g, 693.1 mmol) was added to a solution of N-(3,4-dihydroxyphenethyl) formamide (25.0 g, 137.98 mmol) and triphenylphosphine (109.0 g, 415.6 mmol) in dry THF (250 mL) at 0° C. under nitrogen. DIAD (85.0 g, 420.35 mmol) was added to reaction mixture at 0° C. under nitrogen. Reaction mixture stirred at room temperature for 15 h. After completion of reaction (monitored by TLC), reaction mixture concentrated under reduced pressure at 45° C. The resulting crude was purified by column chromatography on silica gel, eluting with 5% MeOH in MDC, yielding 20 g pure D6-N-(3,4-dimethoxyphenethyl) formamide as a Pale yellow oil (Yield: 70%). Purity by HPLC: 95%

EXAMPLE 3

Preparation of D6-6,7-dimethoxy-3,4-dihydroisoquinoline Hydrochloride

A solution of D6-N-(3,4-dimethoxyphenethyl)formamide (11 g, 51.1 mmol) in dichloromethane (55 mL) was added to a suspension phosporous pentachloride (13.3 g, 63.87 mmol) in dichloromethane (55 mL) at room temperature. Reaction mixture stirred at room temperature for 2 h. After completion of reaction (monitored by TLC), reaction mixture was added to a mixture of crushed ice (55 g) and n-Hexane (55 mL). Aqueous layer was kept aside and organic layer was washed with water (55 mL). The combined aqueous layer was acidified with aqueous potassium hydroxide solution.

Product was extracted with dichloromethane (5×110 mL). The combined organic layer dried over sodium sulphate, filtered and concentrated under reduced pressure at 45° C. to furnish 9.5 g crude product. Crude product was added to a solution of HCl in isopropyl alcohol (75 mL) at room temperature and stirred for 1 hour. The solid was filtered off and washed with Isopropyl alcohol (3×10 mL). The solid isolated was dried at 40° C. for 6 h under reduced pressure, yielding 9.0 g pure D6-6,7-dimethoxy-3,4-dihydroisoquinoline hydrochloride as a pale yellow solid (Yield: 75%). Purity by HPLC: 99%

EXAMPLE 4

Preparation of D6-3-isobutyl-9,10-dimethoxy-3,4,6, 7-tetrahydro-1H-pyrido[2,1-a]isoquinolin-2(11bH)-one Potassium carbonate (17.74 g, 128.36 mmol) was charged slowly to a solution of D6-6,7-dimethoxy-3,4-dihydroisoquinoline hydrochloride (30.0 g, 128.36 mmol) and 2-acetyl-N,N,N,4-tetramethylpentan-1-aminium iodide (48.25 g, 154.04 mmol) in methanol (135.0 mL) and Water (45.0 mL) at room temperature. Reaction mixture stirred at 45° C. for 30 h. After completion of reaction (monitored by TLC), the contents were brought to room temperature and water (90.0 mL) was added into reaction mixture and stirred for 1 hour. The solid separated was filtered off and washed with Water (3×30 mL), dried at 50° C. for 6 h under reduced pressure furnishing 33.0 g crude product. To the crude product obtained was added methanol (130.0 mL) and maintained at 65° C. for 1 hour. The temperature was brought down to 0° C. and stirring continued for 1 hour. The solid separated was filtered off and washed with chilled methanol (2×25.0 mL), dried at 50° C. for 6 hours under reduced pressure, yielding 25.0 g pure D6-3-isobutyl-9,10-dimethoxy-3,4,6,7-tetrahydro-1H-pyrido[2,1-a]isoquinolin-2(11bH)-one as a White solid (Yield: 60%). Purity by HPLC: 99.9%

EXAMPLE 5

Preparation of
D6-6,7-dimethoxy-3,4-dihydroisoquinoline

D4-Methanol (29 g, 803.99 mmol) was added to a solution of 3,4-dihydroisoquinoline-6,7-diol (25 g, 153.21 mmol) and Triphenyl phosphine (121 g, 461.32 mmol) in anhydrous THF (250.0 mL) at 0° C. under nitrogen. DIAD (93 g, 459.92 mmol) was added into reaction mixture at 0° C. and reaction mixture stirred at room temperature for 15 h. After completion of reaction (monitored by TLC), solvent was removed under reduced pressure at 45° C. and the resulting crude was purified by column chromatography on silica gel, eluting with $CH_2Cl_2$:MeOH (95:5), yielding 20.0 g D6-N-(3,4-dimethoxyphenethyl)formamide as a Pale yellow oil (Yield: 66%). Purity by HPLC: 95%

We claim:
1. A process for the preparation of Deutetrabenazine formula I comprising steps of:
   (i) reacting dopamine hydrochloride compound of formula II with ethyl formate in presences of base to obtain N-(2-(3,4-dihydroxy-phenyl)-ethyl)-formamide compound of formula III;
   (ii) cyclization of N-(2-(3,4-dihydroxy-phenyl)-ethyl)-formamide compound of formula III in presences of dehydrating agent to obtain 6,7-dihydroxy-3,4-dihydroisoquinoline compound of formula VII;
   (iii) methylation of 6,7-dihydroxy-3,4-dihydroisoquinoline compound of formula VII with deuterated methanol selected from CD3OD or CD3OH to obtain d6-6,7-Dimethoxy-3,4-dihydroisoquinoline compound of formula V;
   (iv) reacting d6-6,7-Dimethoxy-3,4-dihydroisoquinoline compound of formula V with 2-acetyl-N,N,N,4-tetramethyl-1-pentanaminium iodide compound of formula VI to obtain (RR, SS)-1,3,4,6,7-11 b-Hexahydro-9,10-di (methoxy-d6)-3-(2-methylpropyl)-2H-benzo [a] quinolizin-2-one (Deutetrabenazine) compound of formula I.

2. The process for the preparation of Deutetrabenazine compound of formula I as claimed in claim 1 wherein dehydrating agent selected from the group consisting of phosphorous oxy chloride, phosphorus pentachloride, and thionyl chloride.

3. The process for the preparation of Deutetrabenazine compound of formula I as claimed in claim 1 wherein methylation reaction is carried out in presence of reagent selected from diethyl azodicarboxylate (DEAD), diisopropyl azodicarboxylate (DIAD), di-p-chlorobenzyl azodicarboxylate (DCAD), 1,1'-(Azodicarbonyl)dipiperidine (ADDA), Tetramethyl azodicarboxamide (TMAD in combination with triphenyl phosphine.

4. The process for the preparation of Deutetrabenazine compound of formula I as claimed in claim 1 wherein reaction step (iii) of methylation is carried out in the presences of solvents selected from dichloromethane, ethylene dichloride, carbon tetrachloride, chloroform, tetrahydrofuran, benzene, toluene, N,N-dimethylformamide or mixture thereof.

5. The process for the preparation of Deutetrabenazine compound of formula I as claimed in claim 1 wherein reaction step (iv) is carried out in the presences of solvents selected from n-butanol, isopropanol, n-propanol, ethanol, methanol, water or mixture thereof.

6. The process for the preparation of Deutetrabenazine compound of formula I as claimed in claim 1 wherein base is triethylamine.

* * * * *